United States Patent [19]
Chimeno

[11] 3,984,423
[45] Oct. 5, 1976

[54] PROCESS FOR THE MANUFACTURE OF 3-(N-2',6'-XYLYL)-CARBOXAMIDE-PYRIDONE-2

[76] Inventor: Jose-Alfonso Canicio Chimeno, Plaza Duque de Medinaceli, 4 Barcelona, Spain

[22] Filed: Feb. 12, 1976

[21] Appl. No.: 657,576

Related U.S. Application Data

[63] Continuation-in-part of Ser. No. 565,280, April 4, 1975, abandoned, which is a continuation-in-part of Ser. No. 505,774, Sept. 13, 1974, abandoned.

[30] Foreign Application Priority Data

July 20, 1974 Spain .................................... 428449

[52] U.S. Cl. .................. 260/295.5 A; 260/295.5 T; 424/266

[51] Int. Cl.$^2$ ....................................... C07D 213/56
[58] Field of Search ............................ 260/295.5 A

[56] References Cited
OTHER PUBLICATIONS

Nantka–Namirski, Chem. Abstracts, vol. 66(19), item No. 85678n (May 8, 1967).

*Primary Examiner*—Alan L. Rotman
*Attorney, Agent, or Firm*—Ulle C. Linton

[57] ABSTRACT

The present invention is concerned with a process for producing 3-(N-2'6'-xylyl)-carboxamide-pyridone-2. This compound has anti-inflammatory and analgesic activity.

2 Claims, No Drawings

PROCESS FOR THE MANUFACTURE OF 3-(N-2',6'-XYLYL)-CARBOXAMIDE-PYRIDONE-2

The present application is continuation-in-part of our application Ser. No. 565.280 filed Apr. 4, 1975 now abandoned, which was at its time continuation-in-part of our application Ser. No. 505.774, filed Sept. 13, 1974, now abandoned.

The present invention refers to 3-(N-2',6' xylyl)-carboxamide pyridone-2 formula (I)

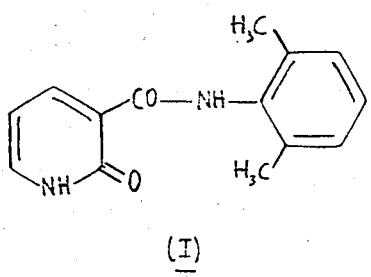

and to a process for its manufacture, that is characterized by using a derivative of the nicotinic acid formula (II) as raw material

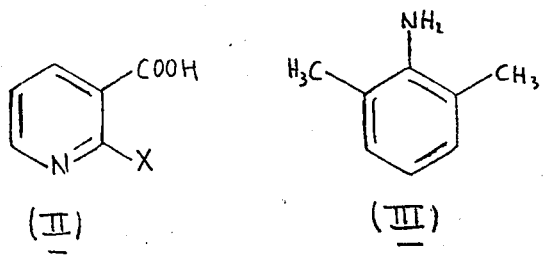

where X can be any halogen, preferably chlorine, that is treated with 2,6-xylidine formula (III)

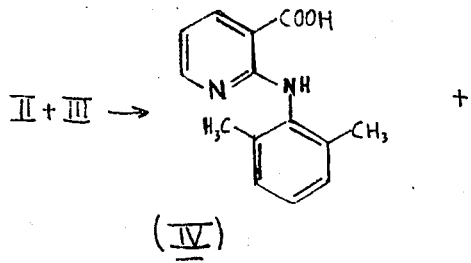

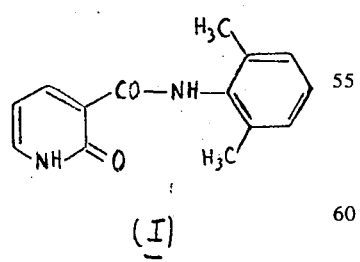

at temperatures between 100° and 160° C, preferably above 140°.

The reaction of the product formula (II) with 2,6-xylidine formula (III) produces a mixture of two products formula (IV) and (I), (I) being the desired product 3-(N-2',6' xylyl)-carboxamide pyridone-2 and (IV) a by product that we do not claim and that is separated from the compound (I) by means of washing of the mixture with an aqueous solution of a strong mineral acid, preferably hydrochloric acid or sulfuric acid, in which the compound formula (IV) is much more soluble, obtaining the pure product (I) after reiterative washings and recrystallizations.

The formation of the compound formula (I) in the reaction is justifiable considering, (according to P. Nantka-Namirrski, Acta Polon. Pharm. (1965), page 428), that 2-chloronicotinic acid heated to 140° C evolves HCl gas while forming the compound formula (V) and (VI) as in the scheme:

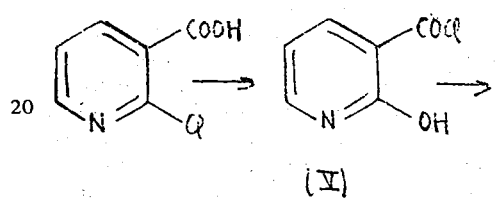

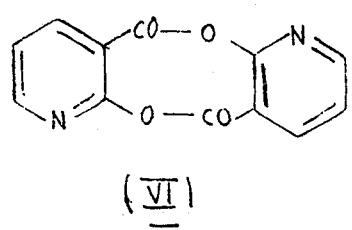

which react very easily with 2,6-xylidine to give the compound formula (I).

In this way it is explained that above 140° C, the reaction of (II) + (III) preferably gives the compound (I) and at lower temperatures the compound of formula (IV) is preferably obtained, by nucleofile substitution of the halogen in the compound (II) by 2,6-xylidine.

The method of preparation of the 3-(N-2',6' xylyl)-carboxamide pyridone-2 formula (I) from a nicotinic acid replaced by a halogen in position 2, preferably 2-chloronicotinic acid, does not exclude the use of activated intermediates. Thus, it is of advantage to prepare 3-(N-2',6' xylyl)-carboxamide pyridone-2 from the acid formula (II) where X is a halogen, preferably chlorine, and preparing "in situ" the acid chloride formula (VII) by means of treatment with thionyl chloride. The compound formula (VII) is treated with 2,6-xylidine formula (II) to obtain the intermediate formula (VIII),

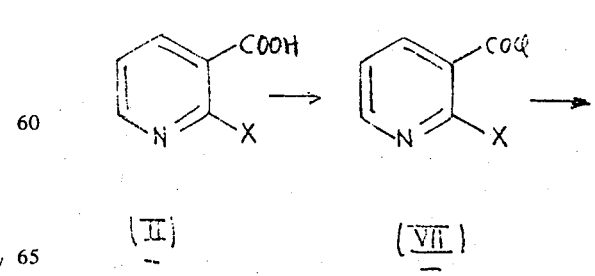

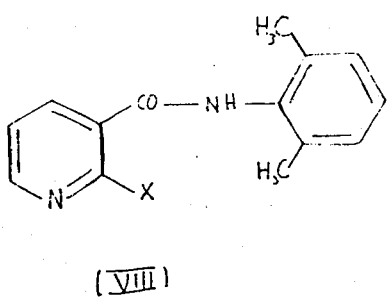

(VIII)

from which is obtained 3-(N-2',6' xylyl) carboxamide pyridone-2 treating it with a alkaline-earth hydroxide in DMSO at a temperature between 110°–170° C.

The formation of the compound formula (I) from the compound formula (VIII), demands therefore the induction, in this case, of the replacement of the halogen in position 2 by an OH group, that was spontaneous in the reaction from the acid formula (II); That means, in fact, the formation of (I) because, as in known, 2-hydroxy pyridines and pyridones-2 like their derivatives are tautomeric entities and therefore quickly interconvertible in a continuous and spontaneous way.

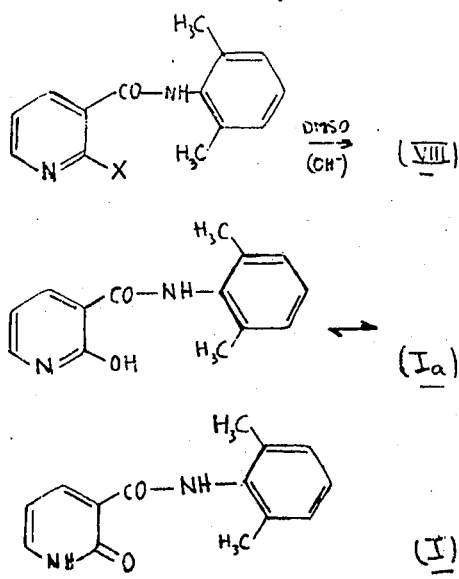

The product of formula (I) is a very stable crystalline white powder, soluble in strong alkalis and insoluble in water and in acids, very resistent to hydrolysis due to steric hinderance of the carboamide group, produced by the two annular methyls placed in position 2',6'. Its melting point is 266° C.

The product, 3-(N-2',6' xylyl)-carboxamide pyridone-2 for which this patent is claimed has pharmacologic and pharmacodinamic properties that give the product therapeutic utility as an anti-inflammatory and analgesic.

The special advantage of this compound resides in the absence of undesirable effects in the gastrointestinal tract and in its low acute toxicity ($LD_{50}$ of the product in rats and mice by oral route is >6.000 mg/Kg. and by intraperitoneal route is >2.000 mg/Kg.)

Analgesic activity was determined in mice by the "Hot Plate" method (Eddy, N.B., Touchberry, C.F., J.Pharm. Exper. Therap. 1950, 98, 121) at 55° C and by the acetic acid — induced writhing (Koster, R., Anderson, N., Fed. Proc. 1959, 18, 412). The product of formula (I) was administered by oral route at different doses (Between 100 and 800 mg/Kg) using morphine, phenylbutazone and acetylsalicylic acid as reference. The effective dose 50 for the product of formula (I) ($ED_{50}$) was calculated to be approximately 75 mg/Kg. in the "Hot Plate" method and approximately 250 mg/Kg. in the "Writing" method.

The anti-inflammatory effect was determined by the carrageenin induced oedema in hind paw method, as in the Winter method (Winter C.A. and cols. "Carrageenin induced oedema in hind paw of the rat as an assay for anti-inflammatory drugs" Proc. Soc. exp. Biol. Med 1962, 111, 544–547). This method was employed in several sets of rats to which were administered different doses of the product (Between 50 and 1600 mg/Kg). Phenylbutazone was used as a reference. ED 50 for product (I) was calculated to be approximately 250 mg/Kg.

The clinical tests carried out until now show that the product, which patent is claimed can be applied to the treatment of accute and chronic inflammations of different etiology, as well as an analgesic in painful processes of different condition.

The drug administration can be carried out under different pharmaceutical forms, mixed with the adequated excipients; such forms can be, capsules, tablets, suppositories, pomade, cream and spray, that's to say: by oral, rectal or topic way in daily doses between 400 and 1600 mg/day.

As a indicatory example of the invention, that in no case must be considered in a restrictive way, we described the following examples:

EXAMPLE 1

0.6 Kg. of 2-chloronicotinic acid and 1 Kg of 2,6-xylidine are heated in a 5 liters cylindric reactor, at 140°. When the solution of the acid in the 2,6-xylidine is produced, a violent reaction takes place with abundant evolution of vapours.

When the strong reaction is finished, the mixture is heated between 160° and 180° C for an hour and a half, letting it cool. 1,5 liters of 10% NaOH are added and strongly stirred to achieve a perfect disgregation of the mass and extracted three times with 1.5 liters of benzene each time. The aqueous phase is acidified to pH = 1. The obtained crude is stirred for a night with HCl 6N. 0.3 Kg of 3-(N-2',6' xilyl)-carboxamide pyridone-2 are obtained, and recrystallizated from ethanol. m.p. 266°–267° C.

EXAMPLE 2 a. 0.64 Kg of 2-chloronicotinic acid are dissolved in 2.37 liters of thionile chloride by means of stirring. When dissolved, the largest possible quantity of thionile chloride is distilled. A liter of benzene is added and most of it is distilled. The residue of this distillation is mixed with another liter of benzene and is added gradually to a boiling solution of 0.5 liters of 2,6-xylidine in 5 liters of benzene. When the addition is finished it's boiled for 15 minutes more, it's cooled and filtered. The mother waters are concentrated to obtain a second fraction. 2',6'-dimethyl anilide of the 2-chloronicotinic acid formula (VIII) is obtained. The yield is 98%. m.p. = 138°–140° C.

b. 1.33 Kg of 2',6'-dimethyl anilide of the 2-chloronicotinic acid and 800 g. of dry soda are dispersed into 2.25 liters of dimethylsulfoxide and are heated to 150° C. After 3 hours the distillation of the dimethylsulfoxide at a reduced pressure is started. Most of dimethylsulfoxide is distilled care being taken to ensure that the height of the stirrer is adequate to avoid as much as possible pyrolysis effects. When the vessel is almost dry, 15 liters of water are added and stirred until complete dissolution. It's acidified to pH = 1 and filtered. 3-(N-2',6' xylyl)-carboxamide pyridone-2 formula (I), m.p. 266°, is obtained and recrystallized from alcohol. The yield is 95%.

Proportions, time, temperature and apparatus used in the described method are independent of the invention's object, supposing that the introduced variations don't affect its essence.

What we claim is:

1. A process for the manufacture of 3-(N-2',6' xylyl-carboxamide pyridone-2 by the reaction of a derivative of the nicotinic acid formula (II) where X is an halogen, preferably chlorine with 2,6-xylidine formula (III), characterised in that the reaction is carried out, with stirring

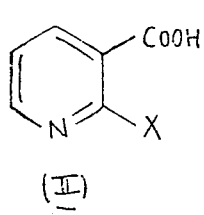

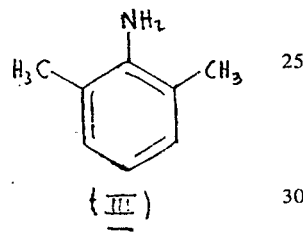

at temperatures between 100° and 160° and preferably above 140°, in excess of 2,6-xylidine, to obtain as main product of the reaction the compound formula (I) by direct condensation and spontaneous replacement of the 2-chloro substituent by 2-OH and also spontaneous subsequent tautomerism, whereby the product is separated from other reaction components due to its insolubility in strong mineral acids, preferably hydrochloric or sulfuric acid.

2. Process as claimed in claim 1 characterized by using in the reaction with 2,6-xylidine an active form of the compound (II) such as the acid halide formula (VIIa) where X and Y are halogens, preferably chlorine; the reaction is carried out in an organic solvent, preferably a hydrocarbon such as benzene, toluene, etc. and without spontaneous replacement of the substituent in position 2,

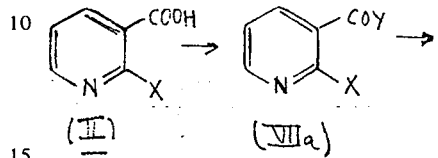

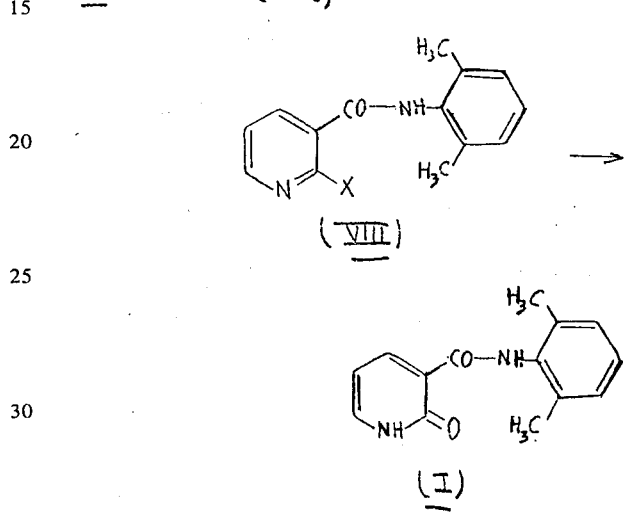

so that the intermediate formula (VIII) is obtained and in which the replacement of the 2-chloro by 2-OH is induced by means of a treatment with DMSO at a temperature between 110°–170° C with an alkaline or alkaline-earth hydroxide to obtain the desired compound formula (I) 3-(N-2',6' xylyl)-carboxamide pyridone-2 by spontaneous tautomerism.

* * * * *